US008694120B2

(12) United States Patent
Murtonen (10) Patent No.: US 8,694,120 B2
(45) Date of Patent: Apr. 8, 2014

(54) SYSTEMS AND METHODS FOR MAKING AND USING ELECTRICAL STIMULATION SYSTEMS WITH IMPROVED RF COMPATIBILITY

(76) Inventor: Salomo Murtonen, Pasadena, CA (US)

( * ) Notice: Subject to any disclaimer, the term of this patent is extended or adjusted under 35 U.S.C. 154(b) by 0 days.

(21) Appl. No.: 13/396,350

(22) Filed: Feb. 14, 2012

(65) Prior Publication Data

US 2012/0215287 A1    Aug. 23, 2012

Related U.S. Application Data

(60) Provisional application No. 61/444,048, filed on Feb. 17, 2011.

(51) Int. Cl.
*A61N 1/00* (2006.01)
(52) U.S. Cl.
USPC .......................................................... 607/62
(58) Field of Classification Search
USPC ................................................ 607/2, 62, 72
See application file for complete search history.

(56) References Cited

U.S. PATENT DOCUMENTS

| | | | |
|---|---|---|---|
| 6,181,969 B1 | 1/2001 | Gord | |
| 6,516,227 B1 * | 2/2003 | Meadows et al. | 607/46 |
| 6,609,029 B1 * | 8/2003 | Mann et al. | 607/37 |
| 6,609,032 B1 | 8/2003 | Woods | |
| 6,741,892 B1 | 5/2004 | Meadows | |
| 7,244,150 B1 | 7/2007 | Brase | |
| 7,437,193 B2 | 10/2008 | Parramon et al. | |
| 7,672,734 B2 | 3/2010 | Anderson | |
| 7,761,165 B1 | 7/2010 | He | |
| 7,949,395 B2 | 5/2011 | Kuzma | |
| 7,974,706 B2 | 7/2011 | Moffitt | |
| 2003/0048621 A1 | 3/2003 | Blood | |
| 2005/0165465 A1 | 7/2005 | Pianca | |
| 2006/0089682 A1 | 4/2006 | Kronich | |
| 2007/0150036 A1 | 6/2007 | Anderson | |
| 2007/0219595 A1 | 9/2007 | He | |
| 2008/0071320 A1 | 3/2008 | Brase | |
| 2008/0183230 A1 | 7/2008 | Kemmetmueller | |
| 2009/0259265 A1 * | 10/2009 | Stevenson et al. | 607/2 |
| 2010/0097079 A1 | 4/2010 | Sheikman | |
| 2010/0114214 A1 | 5/2010 | Morelli | |

FOREIGN PATENT DOCUMENTS

EP    2194548 A2    6/2010
EP    2267894 A2    12/2010

OTHER PUBLICATIONS

International Search Report & Written Opinion, International Application No. PCT/US2012/024972 mailed May 22, 2012.

* cited by examiner

*Primary Examiner* — Christopher D Koharski
*Assistant Examiner* — Nadia Ahmad
(74) *Attorney, Agent, or Firm* — Frommer Lawrence & Haug LLP; Patrick R. Turner (57) ABSTRACT

An implantable control module for an electrical stimulation system includes an electronic subassembly disposed in a sealed conductive housing. A plurality of feedthrough pins extend through the sealed housing and couple connector contact of an external connector to the electronic subassembly. Each of the plurality of conductive pathways electrically couples a different one of the plurality of feedthrough pins to the electronic subassembly. A ground line electrically couples the electronic subassembly to the housing. A capacitive flex circuit is disposed in the housing and couples to each of the feed through pins. For each of the plurality of feedthrough pins the capacitive flex circuit includes a first conductive path electrically coupling the feedthrough pin to a corresponding conductive pathway of the plurality of conductive pathways, and a second conductive path electrically coupling the feedthrough pin to the ground pin.

20 Claims, 9 Drawing Sheets

SYSTEMS AND METHODS FOR MAKING AND USING ELECTRICAL STIMULATION SYSTEMS WITH IMPROVED RF COMPATIBILITY

CROSS-REFERENCE TO RELATED APPLICATIONS

This application claims the benefit under 35 U.S.C. §119 (e) of U.S. Provisional Patent Application Ser. No. 61/444,048 filed on Feb. 17, 2011, which is incorporated herein by reference.

FIELD

The present invention is directed to the area of implantable electrical stimulation systems and methods of making and using the systems. The present invention is also directed to implantable electrical stimulation control modules that modulate undesired propagation of current into electronic systems within the control modules, as well as methods of making and using the control modules and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable control module for an electrical stimulation system includes an electronic subassembly disposed in a sealed housing. The electronic subassembly includes a pulse generator. At least a portion of the housing is formed from a conductive material. A connector is configured and arranged for receiving a lead or lead extension. The connector is disposed outside the sealed housing. The connector includes a plurality of connector contacts. A plurality of feedthrough pins extend through the sealed housing. Each of the plurality of feedthrough pins are electrically coupled to a different one of the connector contacts. A plurality of conductive pathways are disposed in the housing. Each of the plurality of conductive pathways electrically couples a different one of the plurality of feedthrough pins to the electronic subassembly. A ground line electrically couples the electronic subassembly to a ground pin that, in turn, is electrically coupled to a conductive portion of the housing. A capacitive flex circuit is disposed in the housing and is coupled to each of the plurality of feed through pins. For each of the plurality of feedthrough pins the capacitive flex circuit includes a first conductive path electrically coupling the feedthrough pin to a corresponding conductive pathway of the plurality of conductive pathways, and a second conductive path electrically coupling the feedthrough pin to the ground pin. The second conductive path includes a capacitive element.

In another embodiment, an electrical stimulating system includes a control module and a lead. The control module includes an electronic subassembly disposed in a sealed housing. The electronic subassembly includes a pulse generator. At least a portion of the housing is formed from a conductive material. A connector is configured and arranged for receiving a lead or lead extension. The connector is disposed outside the sealed housing. The connector includes a plurality of connector contacts. A plurality of feedthrough pins extend through the sealed housing. Each of the plurality of feedthrough pins are electrically coupled to a different one of the connector contacts. A plurality of conductive pathways are disposed in the housing. Each of the plurality of conductive pathways electrically couples a different one of the plurality of feedthrough pins to the electronic subassembly. A ground line electrically couples the electronic subassembly to a ground pin that, in turn, is electrically coupled to a conductive portion of the housing. A capacitive flex circuit is disposed in the housing and is coupled to each of the plurality of feed through pins. For each of the plurality of feedthrough pins the capacitive flex circuit includes a first conductive path electrically coupling the feedthrough pin to a corresponding conductive pathway of the plurality of conductive pathways, and a second conductive path electrically coupling the feedthrough pin to the ground pin. The second conductive path includes a capacitive element. The lead has a distal end and a proximal end. The lead includes a lead body with a proximal end, a distal end, and a longitudinal length; a plurality of electrodes disposed on the distal end of the lead; a plurality of terminals disposed on the proximal end of the lead; and a plurality of conductors, each conductor electrically coupling at least one of the electrodes to at least one of the terminals.

In yet another embodiment, a method of stimulating patient tissue includes providing an electrical stimulating system. The electrical stimulating system includes a control module and a lead. The control module includes an electronic subassembly disposed in a sealed housing. The electronic subassembly includes a pulse generator. At least a portion of the housing is formed from a conductive material. A connector is configured and arranged for receiving a lead or lead extension. The connector is disposed outside the sealed housing. The connector includes a plurality of connector contacts. A plurality of feedthrough pins extend through the sealed housing. Each of the plurality of feedthrough pins are electrically coupled to a different one of the connector contacts. A plurality of conductive pathways are disposed in the housing. Each of the plurality of conductive pathways electrically couples a different one of the plurality of feedthrough pins to the electronic subassembly. A ground line electrically couples the electronic subassembly to a ground pin that, in turn, is electrically coupled to a conductive portion of the housing. A capacitive flex circuit is disposed in the housing and is coupled to each of the plurality of feed through pins. For each of the plurality of feedthrough pins the capacitive flex circuit includes a first conductive path electrically coupling the feedthrough pin to a corresponding conductive pathway of the plurality of conductive pathways, and a second conductive path electrically coupling the feedthrough pin to the ground pin. The second conductive path includes a capacitive element. The lead has a distal end and a proximal end. The lead includes a lead body with a proximal end, a distal end, and a longitudinal length; a plurality of electrodes disposed on the distal end of the lead; a plurality of terminals disposed on the proximal end of the lead; and a plurality of conductors, each conductor electrically coupling at least one of the electrodes to at least one of the terminals. The electrical stimulating system is implanted into a patient such that the electrodes of the electrical stimulating system are in proximity to patient tissue to be stimulated. Stimulation energy is generated in the control module of the electrical stimulating system. Patient tissue is stimulated using the generated stimulation energy. The stimulation energy is transmitted to the patient tissue through the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation control modules that modulate undesired propagation of current into electronic systems within the control modules, as well as methods of making and using the control modules and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, deep brain stimulation leads, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; and 7,974,706; and U.S. Patent Applications Publication Nos., 2005/0165465, 2007/0150036; 2007/0219595; and 2008/0071320, all of which are incorporated by reference.

Figure 1:
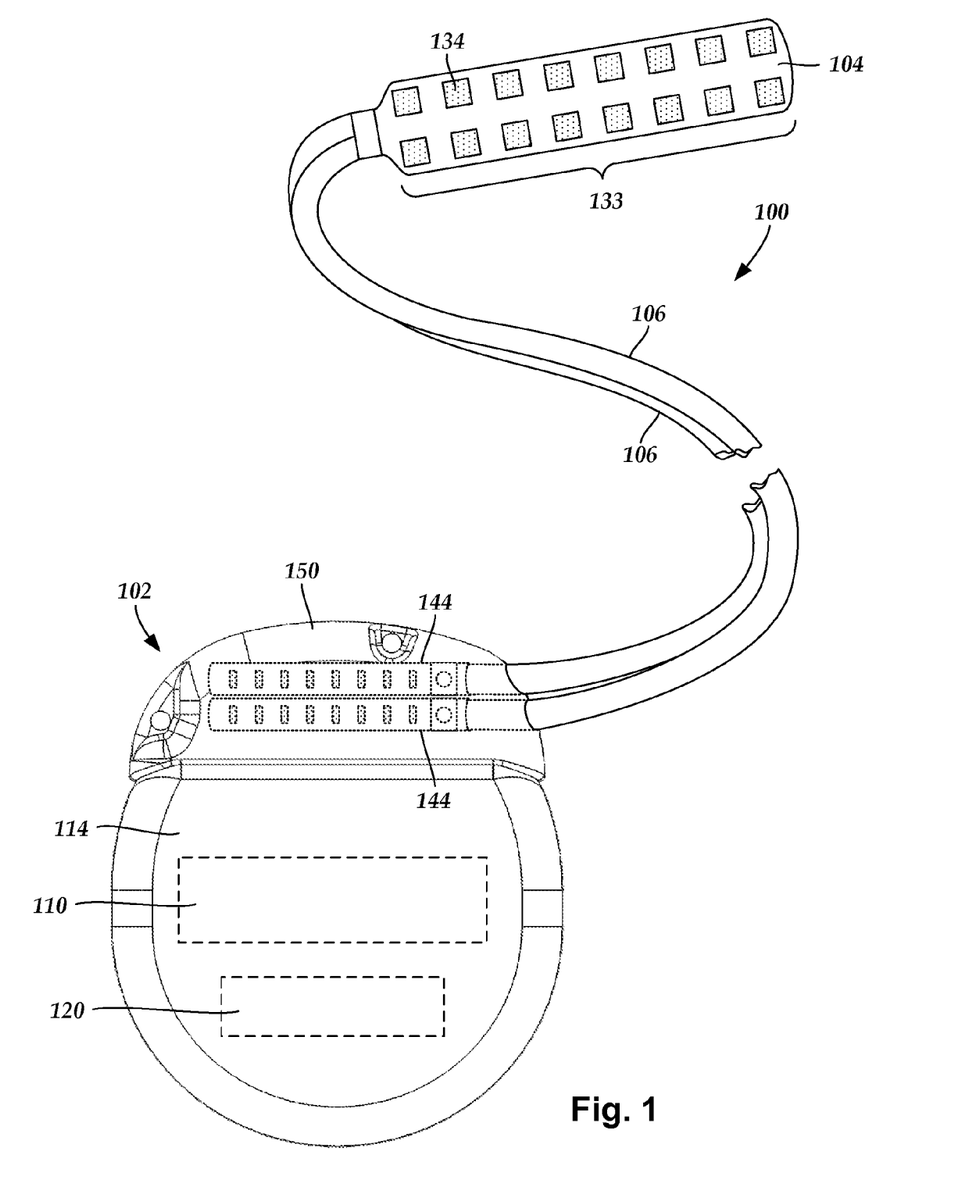
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes a plurality of electrodes 134 that form an array of electrodes 133. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIG. 3A) disposed in the connector assembly 144 and terminals (e.g., 310 in FIG. 3A) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
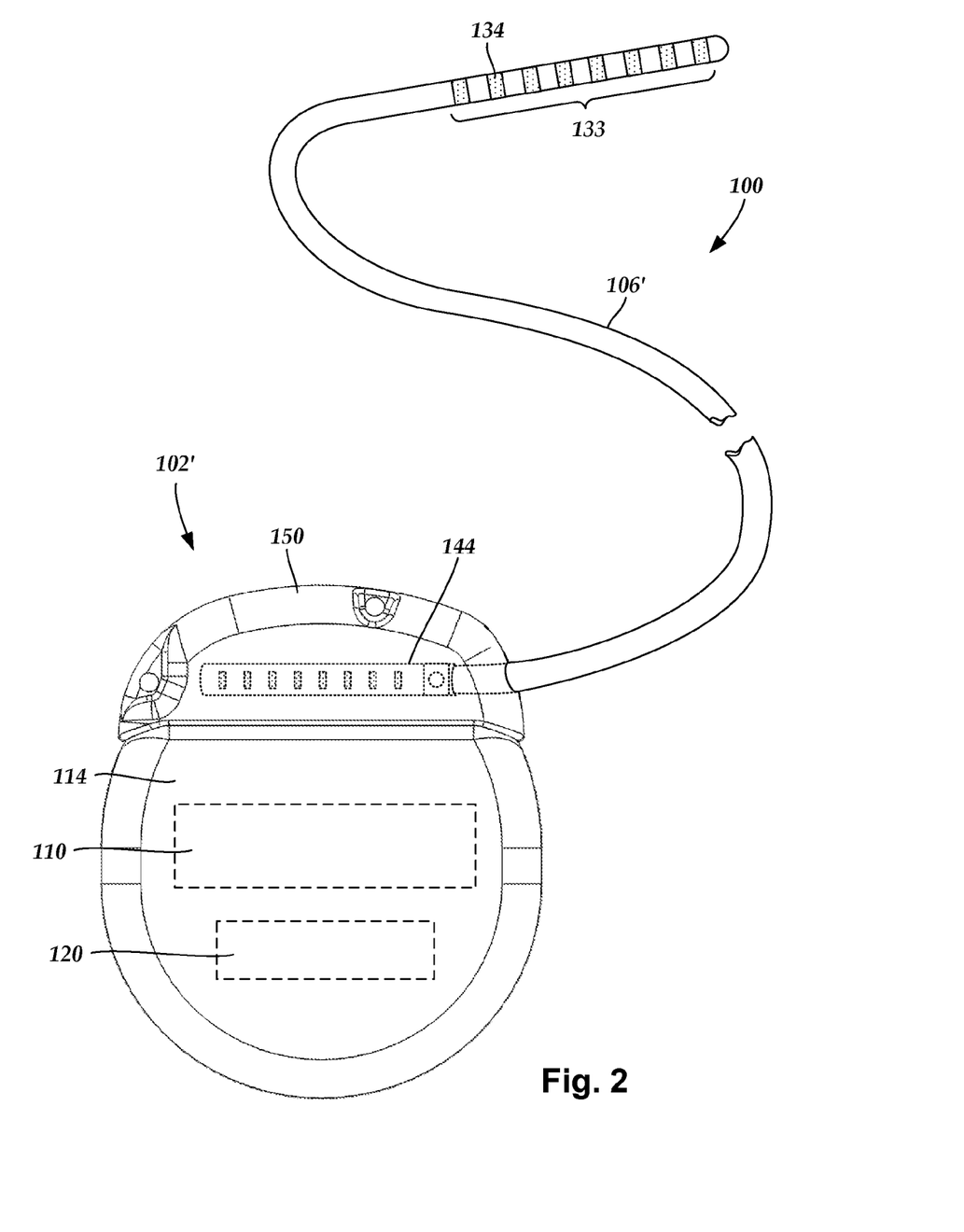
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of a lead body 106' forming a percutaneous lead, as illustrated in FIG. 2. The percutaneous lead may be isodiametric along the length of the lead body 106". The lead body 106' can be coupled with a control module 102' with a single connector assembly 144.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle activation via stimulation of nerves innervating muscle, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 133 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A) are typically disposed at the proximal end of the one or more lead bodies 106 for connection to corresponding conductive contacts (e.g., 316 in FIG. 3A) in connector assemblies (e.g., 144 in FIG. 1) disposed on, for example, the control module 102 (or to other devices, such as conductive contacts on a lead extension, an operating room cable, a splitter, an adaptor, or the like).

Conductive wires (not shown) extend from the terminals (e.g., 310 in FIG. 3A) to the electrodes 134. Typically, one or more electrodes 134 are electrically coupled to a terminal (e.g., 310 in FIG. 3A). In some embodiments, each terminal (e.g., 310 in FIG. 3A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
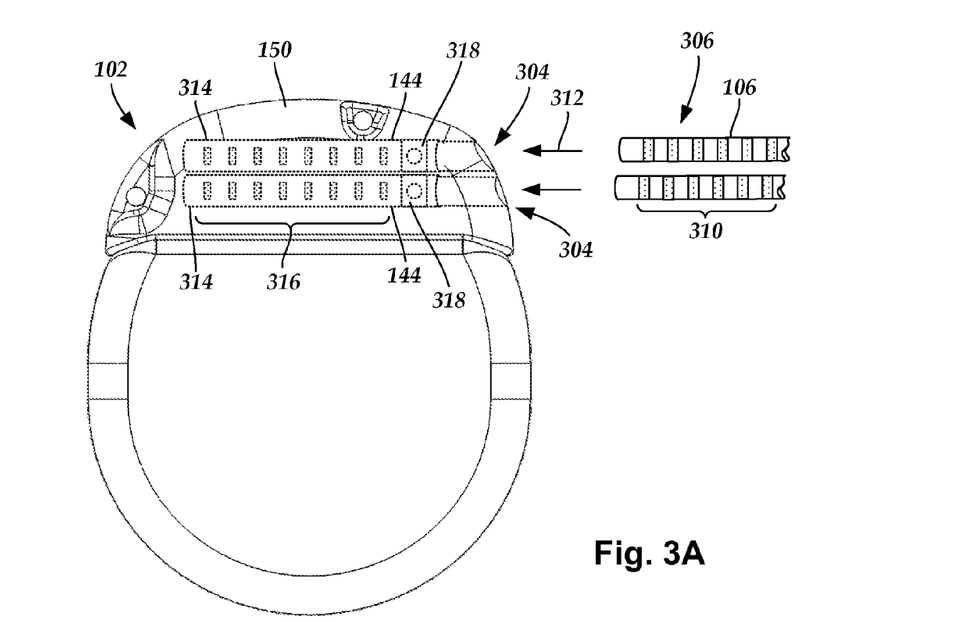
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
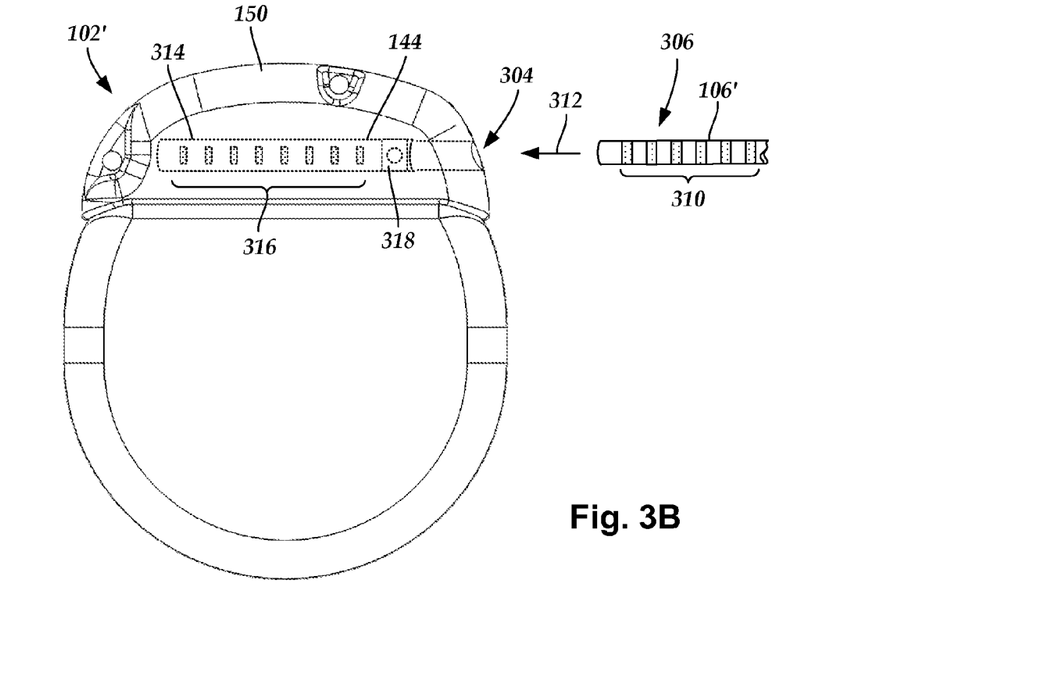
FIG. 3B is a schematic view of one embodiment of a connector assembly disposed in the control module of FIG. 2, the connector assembly configured and arranged to receive the proximal portion of one of the lead body of FIG. 2, according to the invention.

FIG. 3A is a schematic side view of one embodiment of a plurality of connector assemblies 144 disposed on the control module 102. In at least some embodiments, the control module 102 includes two connector assemblies 144. In at least some embodiments, the control module 102 includes four connector assemblies 144. In FIG. 3A, proximal ends 306 of the plurality of lead bodies 106 are shown configured and arranged for insertion to the control module 102. FIG. 3B is a schematic side view of one embodiment of a single connector assembly 144 disposed on the control module 102'. In FIG. 3B, the proximal end 306 of the single lead body 106' is shown configured and arranged for insertion to the control module 102'.

In FIGS. 3A and 3B, the one or more connector assemblies 144 are disposed in the header 150. In at least some embodiments, the header 150 defines one or more ports 304 into which the proximal end(s) 306 of the one or more lead bodies 106/106' with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 106/106' to the connector assembly 144 when the lead body 106/106' is inserted into the connector assembly 144 to prevent undesired detachment of the lead body 106/106' from the connector assembly 144. For example, the retaining element 318 may include an aperture through which a fastener (e.g., a set screw, pin, or the like) may be inserted and secured against an inserted lead body 106/106'.

When the one or more lead bodies 106/106' are inserted into the one or more ports 304, the connector contacts 316 can be aligned with the terminals 310 disposed on the one or more lead bodies 106/106' to electrically couple the control module 102 to the electrodes (134 of FIG. 1) disposed at a distal end of the one or more lead bodies 106. Examples of connector assemblies in control modules are found in, for example, U.S. Pat. No. 7,244,150 and U.S. patent application Ser. No. 11/532,844, which are incorporated by reference.

Figure 3C:
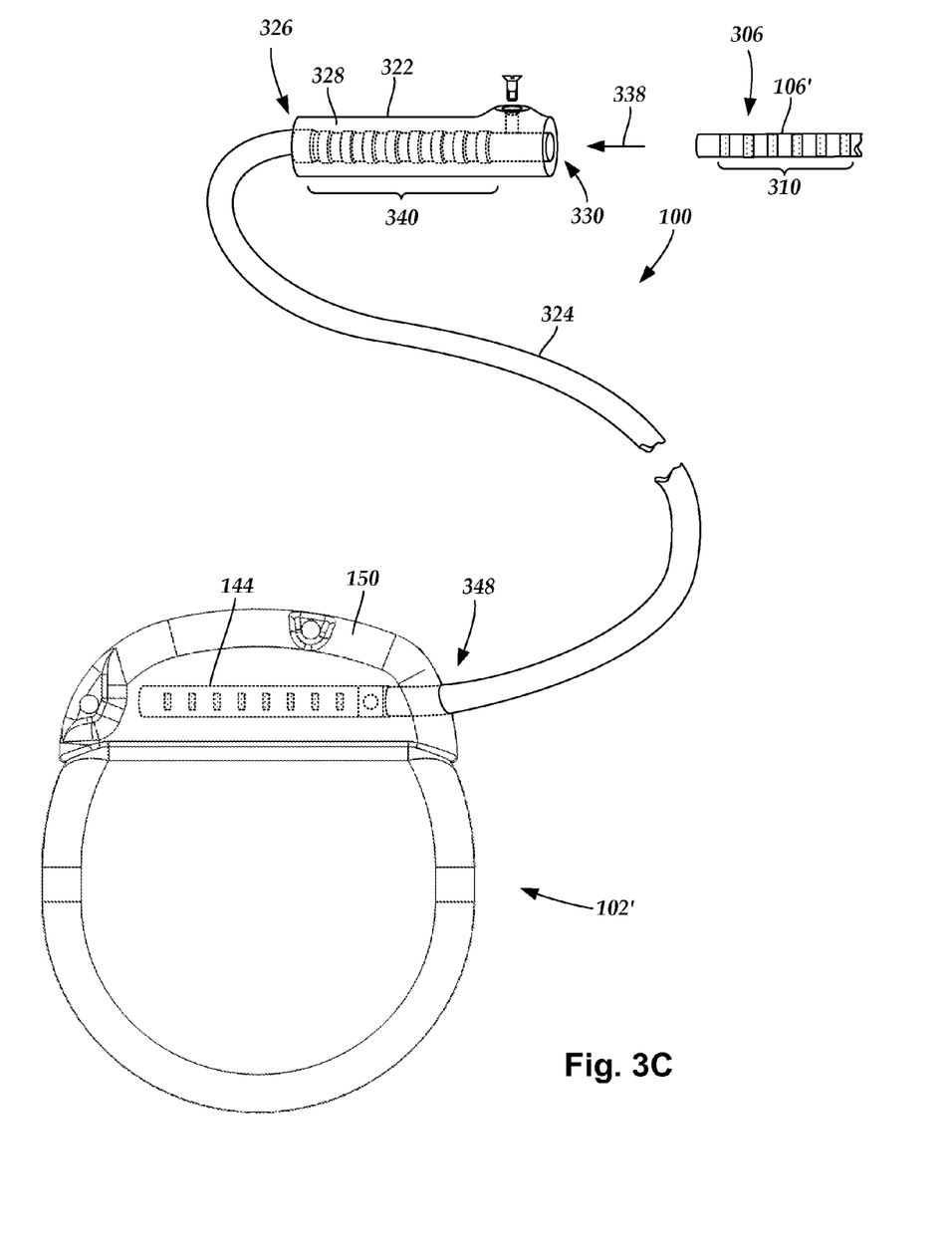
FIG. 3C is a schematic view of one embodiment of a proximal portion of the lead body of FIG. 2, a lead extension, and the control module of FIG. 2, the lead extension configured and arranged to couple the lead body to the control module, according to the invention.

In at least some embodiments, the electrical stimulation system includes one or more lead extensions. The one or more lead bodies 106/106' can be coupled to one or more lead extensions which, in turn, are coupled to the control module 102/102'. In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106' with terminals 310 can be inserted, as shown by directional arrow 338. The lead extension connector assembly 322 also includes a plurality of connector contacts 340. When the lead body 106' is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106'.

The proximal end of a lead extension can be similarly configured and arranged as a proximal end of a lead body. The lead extension 324 may include a plurality of conductive wires (not shown) that electrically couple the connector contacts 340 to terminal on a proximal end 348 of the lead extension 324. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102'.

It will be understood that the control modules 102/102' can receive either lead bodies 106/106' or lead extensions 324. It will also be understood that the electrical stimulation system 100 can include a plurality of lead extensions 224. For example, each of the lead bodies 106 shown in FIGS. 1 and 3A can, alternatively, be coupled to a different lead extension 224 which, in turn, are each coupled to different ports of a two-port control module, such as the control module 102 of FIGS. 1 and 3A.

Conventional electrical stimulation systems may be potentially unsafe for use with magnetic resonance imaging ("MRI") due to the effects of electromagnetic fields in an MRI environment. One mechanism for generating an electrical interaction between the electrical stimulation system and RF irradiation is common-mode coupling of the applied electromagnetic fields. This coupling can be modeled as a series of distributed sources along an elongated conductive structure, such as a lead, or conductors within a lead. Common-mode induced RF currents can reach amplitudes of greater than one ampere in MRI environments. Such currents can cause heating and potentially damaging conditions within electronic circuits.

Some of the deleterious effects of RF irradiation may include, for example, inducing current in the lead, causing undesired heating of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

Figure 4A:
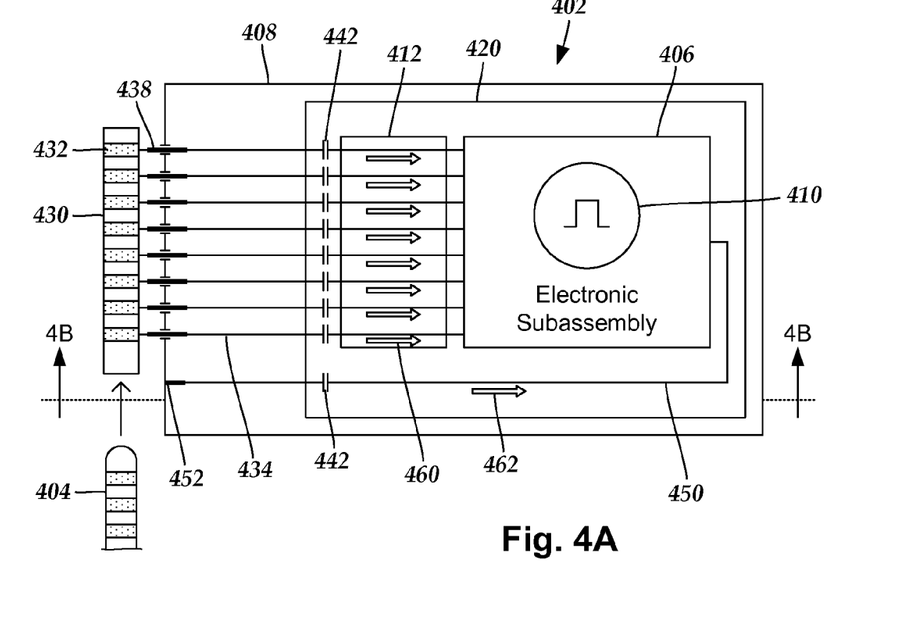
FIG. 4A is a schematic diagram of one embodiment of a control module suitable for providing electrical signals to an electrical stimulation lead, according to the invention.
Figure 4B:
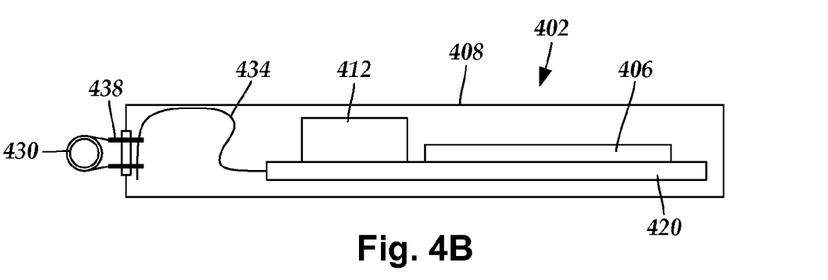
FIG. 4B is a schematic diagram of one embodiment of the control module of FIG. 4A, according to the invention.

FIGS. 4A-4B are schematic diagrams of one embodiment of a control module 402 suitable for providing electrical signals to an electrical stimulation lead 404. The control module 402 includes an electronic subassembly 406 disposed in a sealed housing 408. The electronic subassembly 406 includes a pulse generator 410 for providing electrical signals. The electronic subassembly 406 can be mounted on a printed circuit board ("PCB") 420. Optionally, the control module 402 includes a power source 412 (such as a battery) coupled to the electronic subassembly 406.

A connector assembly 430 is disposed adjacent to the housing 408. A plurality of connector contacts, such as connector contact 432, are disposed in the connector assembly 430. The connector assembly 430 can be configured and arranged to receive one or more leads 404 (see e.g., 310 in FIGS. 3A-3B). Optionally, the connector assembly 430 can be configured and arranged to receive one or more lead extensions (see e.g., 324 in FIG. 3C) in addition to, or in lieu of, one or more leads 404.

The connector contacts 432 of the connector assembly 430 are coupled to the electronic subassembly 406 along conductive pathways, such as conductive pathway 434. In at least some embodiments, the number of conductive pathways is equal to the number of connector contacts 432. The conductive pathways 434 include feedthrough pins, such as feedthrough pin 438, extending through the sealed housing 408. The conductive pathways 434 may additionally include one or more DC blocking capacitors, such as DC blocking capacitor 442. Optionally, at least a portion of the conductive pathways 434 extend along the PCB 420.

The housing 408 is at least partially formed from one or more conductive materials (e.g., one or more metals, alloys, conductive polymers, or the like). The electronic subassembly 406 can be grounded to the housing 408. In FIGS. 4A-4B, the electronic subassembly 406 is shown coupled to a ground line 450 that, in turn, is coupled to a ground pin 452 mounted to a conductive portion of the housing 408. The ground line 450 may include one or more DC blocking capacitors 442.

When the lead 404 (or lead extension) is inserted into the connector assembly 430, and when the electrical stimulation system is implanted into a patient and exposed to RF irradiation (e.g., during an MRI procedure), undesired induced currents can propagate along the lead 404 (and lead extension) and along the conductive pathways 434 of the control module 402 to the electronic subassembly 406, as shown by arrows 460. Additionally, undesired induced currents originating externally from the control module 402 can propagate to the electronic subassembly 406 along the ground line 450, as shown by arrow 462.

To reduce the susceptibility of the electronic subassembly 406 to induced RF currents, one or more current-modulation devices can be disposed in the control module 402. As herein described, one or more current-modulation devices are disposed along the conductive pathways 434 between the electronic subassembly 406 and the connector assembly 430, or disposed along the ground line 450 between the electronic subassembly 406 and the housing 408, or both.

The one or more current-modulation devices are configured and arranged to prevent current above a threshold amount from reaching the electronic subassembly 406 during any condition (e.g., when the current is above a threshold level), or during one or more specific conditions (e.g., when the current is at one or more specific frequencies, when the current is accompanied by an increase of temperature, or the like or combinations thereof). The one or more current-modulation devices can be any type of device suitable for implantation and for modulating current. For example, one or more of the current-modulation devices can be frequency-based, temperature-based, impedance-based, or the like or combinations thereof.

In some embodiments, the one or more current-modulation devices includes a current-limiting element forming a high resistance along a ground line between the electronic subsystem and a ground pin coupled to the housing. In some embodiments, the one or more current-modulation devices can include a capacitive flex circuit disposed between the feedthrough pins and the electronic subassembly. The capacitive flex circuit can electrically couple the feedthrough pins to corresponding conductive pathways, while also electrically coupling the feedthrough pins to the ground pin along a capacitive-element-containing conductive path. Optionally, the capacitive flex circuit electrically couples the feedthrough pins to the ground pin along a capacitive-element-containing conductive path that couples to the ground line.

Figure 5A:
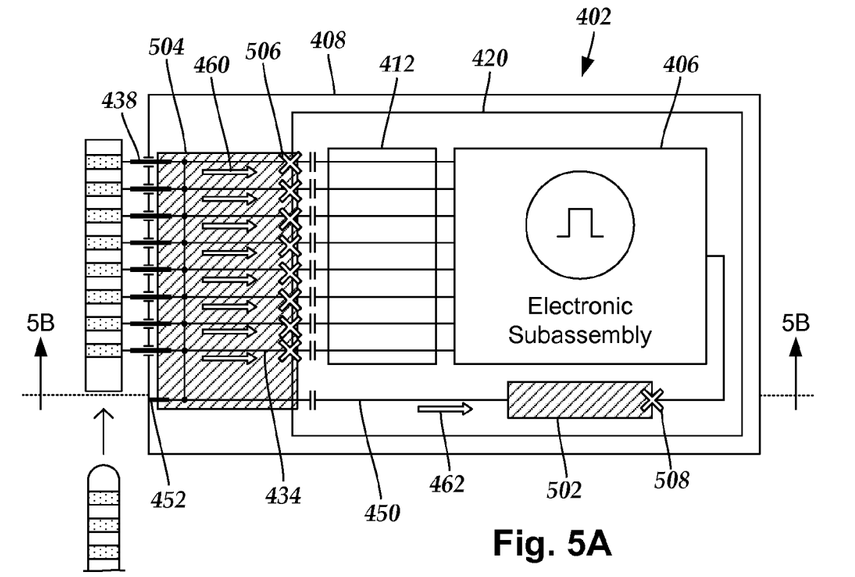
FIG. 5A is a schematic diagram of one embodiment of the control module of FIG. 4A, the control module including a current-limiting element and a capacitive flex circuit, according to the invention.
Figure 5B:
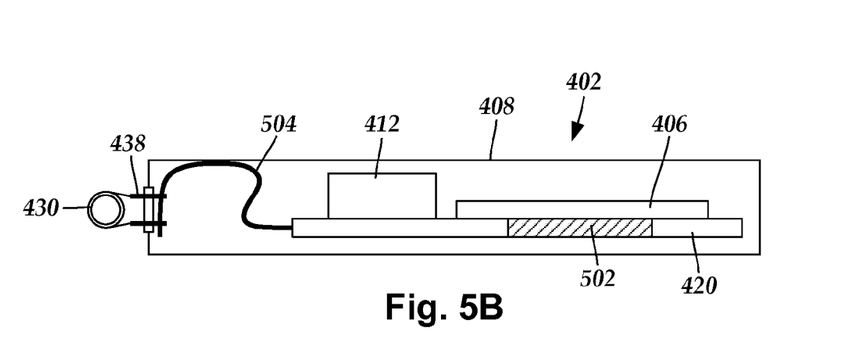
FIG. 5B is a schematic diagram of one embodiment of the control module of FIG. 5A, according to the invention.

FIGS. 5A-5B are schematic diagrams of one embodiment of a current-limiting element 502 and a capacitive flex circuit 504 disposed within the housing 408 of the control module 402. The current-limiting element 502 is disposed along the ground line 450, between the electronic subassembly 406 and the ground pin 452, and is configured and arranged to limit, or even completely block, the propagation of induced current 462 along the ground line 450 of the control module 402 from outside the housing 408 to the electronic subassembly 406, as shown by the "X" 508. The current-limiting element(s) 504 can, optionally, be disposed on the PCB 420.

The current-limiting element 502 can be implemented in any suitable manner. As a first example, the current-limiting element 502 can be implemented as a thermistor. As mentioned above, induced currents can cause undesired heating that may potentially cause tissue damage, undesired or unexpected operation of electronic components, or premature failure of electronic components. Thus, it may be advantageous to use a positive temperature coefficient thermistor, where resistance increases as the surrounding temperature increases. The thermistor can be selected such that the resistance is low at body temperature and is tripped (i.e., the resistance begins to increase) as the internal heat in the thermistor increases above body temperature. The thermistor can be selected such that the resistance increases enough to maintain a safe current level passing through the thermistor to the electronic subsystem 406. When an induced current encounters the thermistor, the heat associated with the induced current trips the thermistor to increase resistance, thereby causing a positive feedback loop as the increased resistance causes additional heat from the induced current.

As another example, the current-suppression unit 504 can be implemented as an inductor. In preferred embodiments, the inductor has an air core so as not to saturate when disposed in proximity to an MRI system. Since the operational frequencies of the electrical stimulation system are much lower than the operational frequencies of a typical MRI system, an inductor can be selected to block the flow of RF energy at the comparatively-high frequencies of the MRI, while causing little or no effect to the comparatively-low operational frequencies of the electrical stimulation system.

As yet another example, the current-suppression unit 504 can be implemented as a resistor. The exemplary implementations of the current-limiting element 502 can be employed individually, or in any combination with one another.

The capacitive flex circuit 504 is disposed at least partially between the feedthrough pins 438 and the PCB 420 and electrically couples the feedthrough pins to corresponding conductive pathways 434. The capacitive flex circuit 504 is configured and arranged to limit, or even completely block, the propagation of induced current 460 along the conductive pathways 434 from the lead 404 to the electronic subassembly 406, as shown by the "X" 506 disposed along each of the conductive pathways 434 at the capacitive flex circuit 504. The blocked current is diverted to the ground pin 452.

Figure 6:
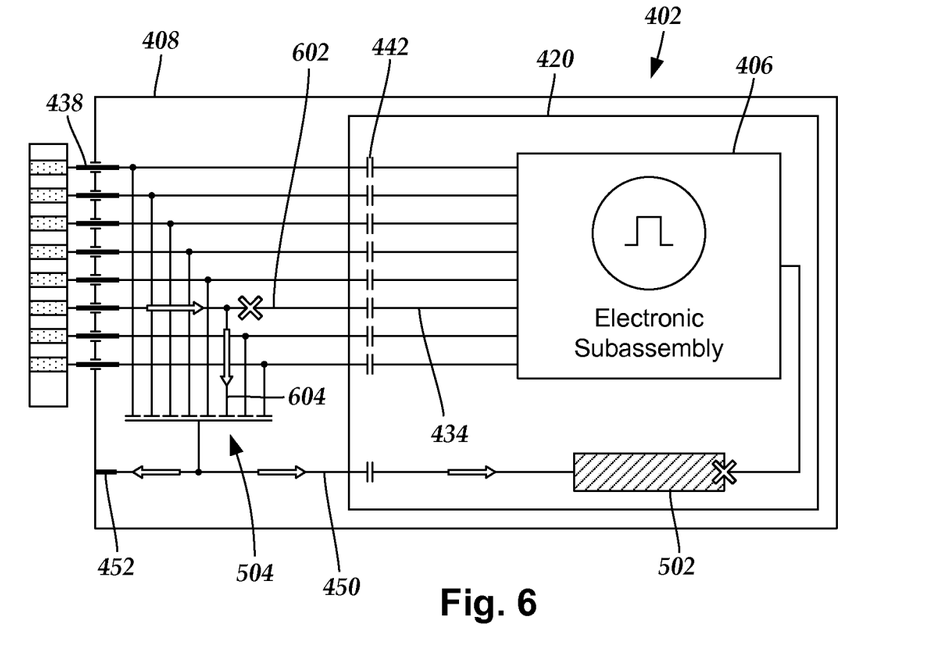
FIG. 6 is a schematic diagram of one embodiment of the current-limiting element of FIG. 5A and the capacitive flex circuit of FIG. 5A disposed within the control module of FIG. 4A, according to the invention.

FIG. 6 is a schematic diagram of one embodiment of the current-limiting element 502 and the capacitive flex circuit 504 disposed within the housing 408 of the control module 402. The capacitive flex circuit 504 includes a plurality of first conductive paths, such as first conductive path 602, coupling the feedthrough pins 438 to the conductive pathways 434, and a plurality of second conductive paths, such as second conductive path 604, coupling the feedthrough pins 438 to the ground pin 452. The second conductive paths 604 include capacitive elements. The capacitive elements of the second conductive paths 604, consequently, are in parallel with the DC blocking capacitors 442.

As mentioned above, the operational frequencies of the control module 402 are significantly lower than those of a typical MRI device. Consequently, the capacitive flex circuit 504 can use capacitive elements that are selected such that undesired current with frequencies commonly experienced during exposure to MRI (e.g., 64 MHz, 128 MHz, or the like) preferentially propagates along the second conductive path 604 (as shown in FIG. 6 by the arrow along the second conductive path 604 and the "X" along the first conductive path 602), while current at or around the operational frequencies of the electrical stimulation system preferentially propagates along the first conductive path 602.

Current propagating along the second conductive path 604 can be routed directly to the ground pin 452, or can be routed to the ground pin 452 via the ground line 450. When the second conductive path 604 is coupled to the ground line 450, the current-limiting element 502 blocks propagation of the undesired current along the ground line 450 to the electronic subassembly 406, thereby causing the undesired current to, instead, propagate along the ground line 450 to the ground pin 452, as shown by arrows on FIG. 6.

The capacitive flex circuit 504 can be implemented in any suitable manner to modulate current on, or around, a specific frequency, or frequency range, or frequencies above a threshold frequency. For example, the capacitive flex circuit 504 can be implemented as one or more separate capacitors coupled to each individual feedthrough pin 438.

In some embodiments, the capacitive flex circuit 504 is implemented as a multi-layered structure that includes one or more dielectrics sandwiched between a plurality of top plates and one or more bottom plates. It may be advantageous to embed capacitance within the structure of a flex circuit. Embedding capacitance within the structure of a flex circuit may enable current modulation without needing to increase the size of the PCB 420 to accommodate additional capacitors. Embedding capacitance within the structure of a flex circuit may also reduce the risk of failure due to loss of electrical connection between capacitors and conductors by reducing the number of capacitors.

Figure 7A:
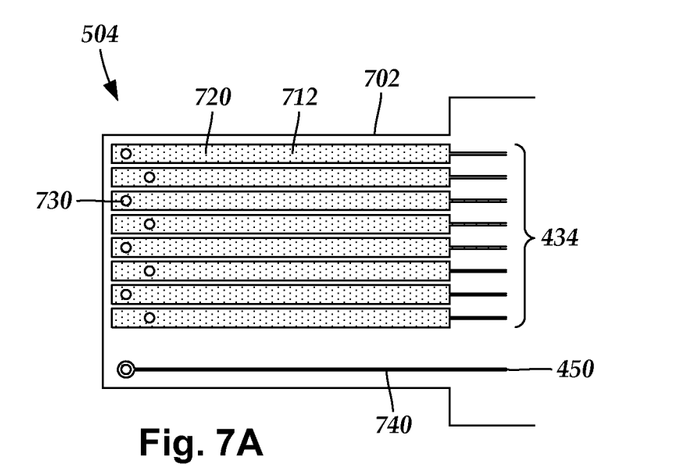
FIG. 7A is a schematic top view of one embodiment of a portion of a top layer of the capacitive flex circuit of FIG. 5A, according to the invention.
Figure 7B:
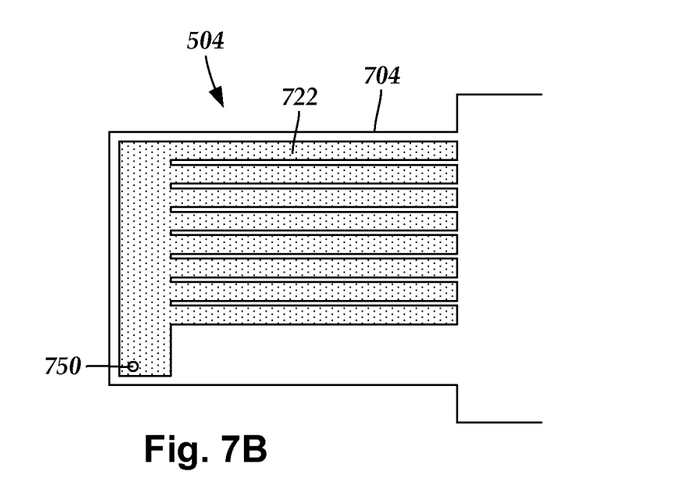
FIG. 7B is a schematic top view of one embodiment of a portion of a bottom layer of the capacitive flex circuit of FIG. 5A, according to the invention.

FIG. 7A is a schematic top view of one embodiment of an exemplary top layer 702 of the capacitive flex circuit 504. FIG. 7B is a schematic top view of one embodiment of an exemplary bottom layer 704 of the capacitive flex circuit 504.

The top layer 702 includes a plurality of electrode traces, such as electrode trace 712. The electrode traces 712 can couple to the conductive pathways 434. Portions of the electrode traces 712 can also operate as top plates 720 of capacitive elements. The bottom layer 704 includes one or more bottom plates 722 which correspond to the one or more top plates 720. In some embodiments, each top plate 720 is coupled to a different feedthrough pin 438. In some embodiments, a single bottom plate 722 is used for each of the top plates 720. The top layer 702 can be overlaid onto the bottom layer 704 such that the corresponding plates 720, 722 at least partially align with one another. A dielectric layer (not shown) is disposed (e.g., sandwiched) between the top and bottom layers 702 and 704, respectively.

One end of each of the electrode traces 712 may include a coupling aperture, such as coupling aperture 730, configured and arranged to electrically couple with a corresponding feedthrough pin 438. The opposing ends of the electrode traces 712 are configured and arranged to electrically couple to the conductive pathways 434 which, in turn, couple to the electronic subassembly 406.

The top layer 702 also includes a ground trace 740 electrically coupling the ground line 450 to the ground pin 452. The ground line 450, in turn, is electrically coupled to the electronic subassembly 406. The bottom layer 704 includes a coupling aperture 750 configured and arranged to couple with the ground pin 452.

The control module 402, connector assembly 430, and capacitive flex circuit 504 shown in FIGS. 4A-7B are shown for an 8-electrode lead. It will be understood that the control module 402, connector assembly 430, and capacitive flex circuit 504 can be used with any electrical stimulation systems having any suitable number of electrodes including, for example, one, two, three, four, five, six, seven, eight, nine, ten, eleven, twelve, thirteen, fourteen, fifteen, sixteen, twenty-four, thirty-two, or more electrodes.

Figure 8:
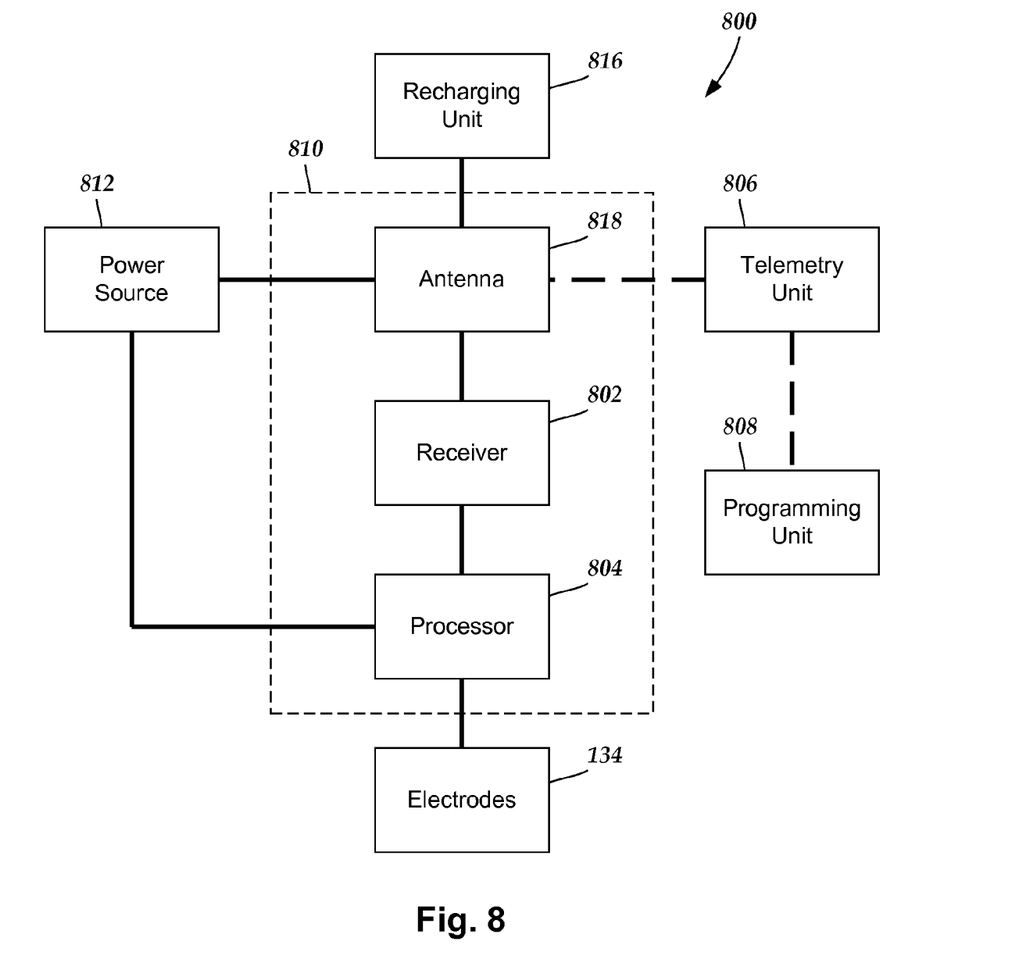
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable control module for an electrical stimulation system, the control module comprising:
    an electronic subassembly disposed in a sealed housing, the electronic subassembly comprising a pulse generator, wherein at least a portion of the housing is formed from a conductive material;
    a connector configured and arranged for receiving a lead or lead extension, the connector disposed outside the sealed housing, wherein the connector comprises a plurality of connector contacts;
    a plurality of feedthrough pins extending through the sealed housing, each of the plurality of feedthrough pins being electrically coupled to a different one of the connector contacts;
    a plurality of conductive pathways disposed in the housing, each of the plurality of conductive pathways electrically coupling a different one of the plurality of feedthrough pins to the electronic subassembly;
    a ground line electrically coupling the electronic subassembly to a ground pin that, in turn, is electrically coupled to a conductive portion of the housing; and
    a capacitive flex circuit disposed in the housing, the capacitive flex circuit comprising a multi-layered flexible substrate comprising a top layer, a bottom layer, and a dielectric layer disposed between the top layer and the bottom layer, wherein the top layer comprises a plurality of first conductive traces electrically coupling the plurality of feedthrough pins to the plurality of conductive pathways, and wherein the bottom layer comprises a plurality of second conductive traces electrically coupling the plurality of first conductive traces to the ground pin.

2. The control module of claim 1, wherein the plurality of first conductive traces comprises a plurality of first conductive plates, and wherein each of the plurality of first conductive plates is electrically coupled to a different feedthrough pin of the plurality of feedthrough pins.

3. The control module of claim 1, wherein the capacitive flex circuit is configured and arranged such that when current within a first frequency range propagates into the housing along at least one of the feedthrough pins the current preferentially propagates along the first conductive trace.

4. The control module of claim 3, wherein the capacitive flex circuit is configured and arranged such that when current within a second frequency range that is different from the first frequency range propagates into the housing along at least one of the feedthrough pins the current preferentially propagates along the second conductive trace.

5. The control module of claim 1, wherein a DC blocking capacitor is disposed along each of the plurality of conductive pathways.

6. The control module of claim 1, further comprising a current-limiting element disposed on the ground line between the electronic subassembly and the ground pin, the current-limiting element configured and arranged to prevent current above a threshold current level from propagating along the ground line into the electronic subassembly.

7. The control module of claim 6, wherein the resistance of the current-limiting element increases when the temperature at the current-limiting element increases above body temperature.

8. The control module of claim 6, wherein the current-limiting element comprises a positive temperature coefficient thermistor.

9. The control module of claim 6, wherein the current-limiting element comprises an inductor.

10. The control module of claim 9, wherein the inductor is an air core inductor.

11. The control module of claim 6, wherein the current-limiting element comprises a resistor.

12. The control module of claim 1, wherein the electronic subassembly is disposed on a printed circuit board.

13. The control module of claim 1, further comprising a power source coupled to the electronic subassembly.

14. An electrical stimulating system comprising:
    the control module of claim 1; and
    a lead having a distal end and a proximal end, the lead comprising
        a lead body with a proximal end, a distal end, and a longitudinal length,
        a plurality of electrodes disposed on the distal end of the lead,
        a plurality of terminals disposed on the proximal end of the lead, and
        a plurality of conductors, each conductor electrically coupling at least one of the electrodes to at least one of the terminals.

15. The electrical stimulating system of claim 14, wherein the plurality of connector contacts disposed in the connector are configured and arranged to electrically couple with the plurality of terminals disposed on the proximal end of the lead.

16. The electrical stimulating system of claim 14, further comprising a lead extension having a proximal end and a distal end, the lead extension comprising
    a lead extension connector disposed at the proximal end of the lead extension, and
    a plurality of lead extension terminals disposed at the proximal end of the lead extension.

17. The electrical stimulating system of claim 16, wherein the lead extension connector is configured and arranged to receive the plurality of lead terminals.

18. The electrical stimulating system of claim 16, wherein the plurality of connector contacts disposed in the control module connector are configured and arranged to electrically couple with the plurality of lead extension terminals disposed on the proximal end of the lead extension.

19. A method of stimulating patient tissue comprising:
    providing the electrical stimulating system of claim 14;
    implanting the electrical stimulating system into a patient such that the electrodes of the electrical stimulating system are in proximity to patient tissue to be stimulated;
    generating stimulation energy in the control module of the electrical stimulating system; and
    stimulating patient tissue using the generated stimulation energy, the stimulation energy transmitting to the patient tissue through the electrodes.

20. The control module of claim 2, wherein the plurality of second conductive traces comprises at least one second conductive plate, wherein the at least one second conductive plate is electrically coupled to the ground pin, and wherein the dielectric layer is sandwiched between the plurality of first conductive plates and the at least one second conductive plate.

* * * * *